(12) United States Patent
Moore et al.

(10) Patent No.: US 6,300,301 B1
(45) Date of Patent: Oct. 9, 2001

(54) CLEANSING PREPARATION AND ARTICLES COMPRISING A CLEANSING PREPARATION

(75) Inventors: Katherine Louise Heinicke Moore, Konigstein; Michael Scott Bogdanski, Bonn, both of (DE); Paul Ralph Bunke, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/566,785

(22) Filed: May 9, 2000

Related U.S. Application Data

(62) Division of application No. 08/695,160, filed on Aug. 7, 1996, now Pat. No. 6,063,746.

(30) Foreign Application Priority Data

Aug. 14, 1995 (EP) .................................................. 95305650

(51) Int. Cl.[7] .............................. C11D 3/48; C11D 13/10
(52) U.S. Cl. ...................... 510/417; 510/130; 424/78.03; 516/53
(58) Field of Search ................................... 510/226, 221, 510/106, 452, 340, 223, 417, 130; 134/276, 1, 2, 6, 27, 40; 424/226.1, 229.1, 265.1, 401, 450, 49, 70.1, 70.12, 78.03; 516/53

(56) References Cited

U.S. PATENT DOCUMENTS

| | | | |
|---|---|---|---|
| 3,829,563 | 8/1974 | Barry et al. | 424/70 |
| 4,184,978 | 1/1980 | France et al. | 252/309 |
| 4,263,284 | 4/1981 | Schreuder | 424/180 |
| 4,637,933 | 1/1987 | Zabotto neé Arribau et al. | 424/131 |
| 4,971,788 | 11/1990 | Tabibi et al. | 424/49 |
| 5,043,155 | 8/1991 | Puchalski et al. | 424/78 |
| 5,230,821 | 7/1993 | Larson et al. | 252/170 |
| 5,318,777 | 6/1994 | Mottier et al. | 424/401 |
| 5,372,637 | * 12/1994 | Dwight, Jr. . | |
| 5,436,007 | 7/1995 | Hartung et al. | 424/402 |
| 5,498,406 | 3/1996 | Nearn et al. | 424/59 |
| 5,534,265 | 7/1996 | Fowler et al. | 424/489 |
| 5,585,104 | 12/1996 | Ha et al. | 424/401 |
| 5,925,341 | * 7/1999 | Cervantes et al. . | |
| 6,063,746 | * 5/2000 | Moore et al. . | |

FOREIGN PATENT DOCUMENTS

| | | |
|---|---|---|
| 0 328 355 A2 | 8/1989 | (EP) . |
| 0 579 455 A1 | 1/1994 | (EP) . |
| 0 613 675 A1 | 9/1994 | (EP) . |
| 0 615 741 A1 | 9/1994 | (EP) . |
| 0759291 | * 8/1995 | (EP) . |
| 0 759 291 A1 | 2/1997 | (EP) . |
| 2-54800 | 9/1987 | (JP) . |
| WO 93/21293 | 10/1993 | (WO) . |

OTHER PUBLICATIONS

Charles Wait (Process Plant) Ltd. Product Literature—Homogenisers.*

* cited by examiner

Primary Examiner—Margaret Einsmann
Assistant Examiner—Gregory E. Webb
(74) Attorney, Agent, or Firm—Roddy M. Bullock; Edward J. Milbrada; Eileen L. Hughett

(57) ABSTRACT

A cleansing preparation is provided in the form of an oil-in-water emulsion. The oil phase particles have a median particle diameter by volume of not more than 1 $\mu$m, and a preservative is present in at least the aqueous phase. A method is described of making this preparation, in which a coarse emulsion is formed, the coarse emulsion is homogenized, and the homogenized emulsion is diluted by an aqueous dilution liquid containing the preservative. Cleansing articles, for example baby wipes can be made in which a substrate carries the cleansing preparation.

5 Claims, 7 Drawing Sheets

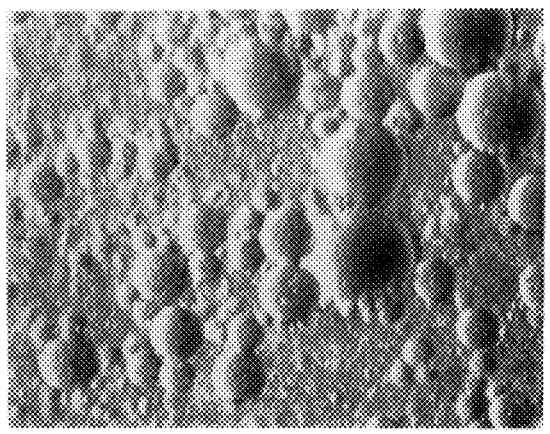 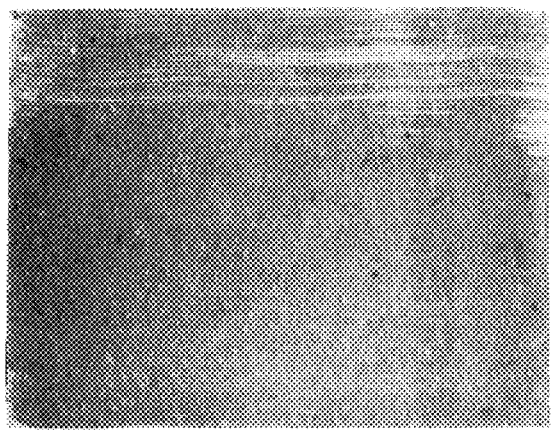
Fig. 7   40 μm          40 μm   Fig. 8

CLEANSING PREPARATION AND ARTICLES COMPRISING A CLEANSING PREPARATION

This application is a divisional application of U.S. Ser. No. 08/695,160, filed Aug. 7, 1996 now U.S. Pat. No. 6,063,746 in the names of Katherine Louise Heinicke Moore, Michael Scott Bogdanski, and Paul Ralph Bunke.

This invention relates to a cleansing preparation, a process for producing such a preparation, and cleansing articles provided with such a preparation. For reasons which will become apparent from the ensuing description, the preparation of the invention is referred to herein as a lotion.

The invention particularly concerned with a lotion suitable for use as a baby wipe lotion, and to baby wipes containing such a lotion. However, it is to be understood that the invention is of wider application than this, and that it encompasses a lotion which is intended to be provided to a user in the form of a liquid, for example in a container of glass, plastics or other materials, for application to the skin either directly from the container or by use of a cleansing member, for example one which includes or consists of cotton wool. The invention also encompasses cleansing articles other than baby wipes, for example wipes commonly used when travelling, in restaurants, in domestic situations and elsewhere. For simplicity, however, the ensuing description will concentrate on the application of the invention in the field of baby wipes.

Conventionally, a baby wipe consists of a small sheet of fibrous material impregnated with an aqueous cleansing preparation. Such wipes have been found to be very acceptable as a means of cleansing urine and bowel motions from a baby's skin, for example in the course of changing the baby's diaper. However, although effective for the purpose of cleansing, such wipes do not, normally, of themselves, provide any protection for the skin against the effects of subsequent wetting or soiling, and it is therefore common practice, after using the baby wipe, to apply an oil-based material, for example in the form of a cream.

EP-A-328355 and EP-A-0613675 describe an oil-in-water emulsion for use, inter alia, in baby wipes. It is noted, however, that no reference is made in either to the size of the oil particles in the emulsion, a matter which is discussed below as being of considerable significance. However, in the case of EP-A-328355, it is specifically stated that polymeric emulsification is used.

It is an object of the present invention to provide, inter alia, a baby wipe, and a liquid preparation for use therein which both has an effective cleansing action and which contains an oil to afford protection to the skin. The liquid preparation is to be stable, so as to permit storage thereof and, more importantly, the storage of baby wipes impregnated therewith, for extended periods without deterioration. The liquid preparation should also be such that, despite the presence of the oil, it does not give rise to an unacceptably sticky feel on the skin, bearing in mind that some of the material will inevitably end up on the skin of the person handling the baby, rather than on the baby's own skin.

As in the case of the product described in EP-A-328355 and EP-A-0623675 mentioned above, the approach adopted in the present invention is to use an oil-in-water emulsion, in which there is a high proportion of water to provide the cleansing action, and in which the droplets of oil provide the desired skin protection. However, one of the major problems encountered in employing this approach is that of making the emulsion sufficiently stable.

Some known cosmetic and toiletry products which use such emulsions achieve stability of the emulsion by adding materials to the aqueous phase to give it a high viscosity. However, that option is not desirable where baby wipes are concerned, since the increased viscosity of the aqueous phase would both impair the cleansing action and make it difficult to apply the liquid to the fibrous sheets. Polymeric emulsification, as described in EP-A-328355, is also disadvantageous because of the increase in viscosity which it produces.

According to the present invention there is provided a cleansing preparation in the form of an emulsion having a continuous aqueous phase and a discontinuous oil phase, the preparation comprising a preservative system which is present at least in the aqueous phase, the oil phase consisting of particles having a median particle diameter by volume of not more than 1 $\mu$m. The median particle size is preferably not more than 0.5 $\mu$m, more preferably not more than 0.3 $\mu$m, and most preferably not more than 0.2 $\mu$m. At least about 98% of the particle volume is preferably in the form of particles having a diameter of not more than 2 $\mu$m, more preferably not more than 1 $\mu$m, and most preferably not more than 0.5 $\mu$m. The preparation preferably has a viscosity less than 150 mPa.s, more preferably less than 50 mPa.s, and most preferably less than 5 mpa.s. The preservative system preferably comprises phenoxyethanol, preferably in an amount equal to less than 1%, more preferably less than 0.8%, by weight based on the total weight of the preparation. Another preferable component of the preservative system, which may be used together with the phenoxyethanol, is a paraben compound.

The invention further provides a method of producing a cleansing preparation as defined above or a concentrate therefor, comprising the steps of forming a coarse emulsion having a continuous aqueous phase and a discontinuous oil phase, and passing at least substantially the whole of the coarse emulsion through a homogenizer at least once so that the oil phase in the homogenized emulsion consists of particles having the desired median particle diameter.

The step of passing the coarse emulsion through the homogenizer may be carried out a plurality of times, and is preferably carried out using a high pressure homogenizer. This pressure is preferably in excess of 100 bar, more preferably at least 175 bar.

In a preferred embodiment, the method further comprises the step of diluting the homogenized emulsion with an aqueous dilution liquid, and the dilution liquid preferably comprises at least part of the preservative system. The dilution liquid may comprise a first part of the preservative system, with the remainder of the preservative system being added after dilution, in which case the remainder of the preservative system preferably comprises the component or components thereof having the greatest ratio of oil solubility. In one embodiment of the method of the invention, the said first part of the preservative system comprises the phenoxyethanol, and the said remainder of the preservative system comprises at least one paraben compound.

The invention also provides a cleansing article which comprises a substrate which carries a cleansing preparation according to the invention or a cleansing preparation produced according to the method of the invention. The substrate is preferably flexible, and is preferably non-woven.

In this description, various chemical substances will be referred to using nomenclature commonly used in the industry and set out in the International Cosmetic Ingredient Dictionary (5th edition, 1993) published by The Cosmetic, Toiletry and Fragrance Association, Inc., 1110, 17th Street, N.W., Suite 300, Washington, D.C. 20036-4702, USA.

In the accompanying drawings:

FIGS. 7 and 8 are photomicrographs of a coarse emulsion and a homogenized emulsion respectively;

Figure 1:
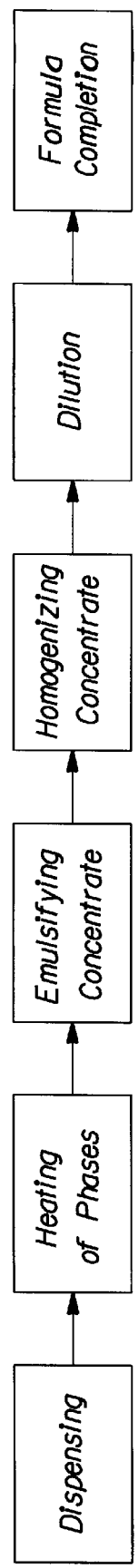
FIG. 1 shows diagrammatically the steps involved in carrying out one embodiment of a process according to the present invention.

A more detailed description will now be given of the steps involved in carrying out one form of the process according to the present invention, with reference to FIG. 1.

Where compositions are given in parts these are parts by weight.

The steps are as follows:

Step 1: Dispensing

An oil phase and a water phase are prepared separately. In this example, these consist of the following:

Oil phase

Mineral Oil (2 parts)

Dicaprylyl Ether (1 part)

Caprylic/Capric Triglyceride (1 part)

Ceteareth-12 (1 part)

Ceteareth-20 (1 part)

TOTAL 6 parts

Water Phase

Water, purified (12 parts)

In the oil phase, Dicaprylyl Ether and Caprylic/Capric Triglyceride are oils and are included with the Mineral Oil to give an appropriate sensation to the user. Ceteareth-12 and Ceteareth-20, are surfactants, and are provided both to enable an emulsion to be formed when the oil and water phases are mixed in step 3 below, and to act as cleansing agents. It will be appreciated that, as with all the components described herein, alternatives can be used. For example ionic surfactants might be used in place of Ceteareth-12 and -20. which are non-ionic.

As will be apparent from what is said below, the 6 parts of the oil phase correspond in the final product to 6% of the total composition. More or less than this amount can be used, though the amount is preferably from 1 to 10%. It will be seen that the total of the oil and water phases at this stage amounts in this example to 18 parts. If the amount of the oil phase is altered, it is preferable that the amount of the water phase should be altered also. Preferably, the ratio of the weight of the aqueous phase to the weight of the oil phase, is at least 0.5 to 1, more preferably at least 1 to 1.

Step 2: Heating of Phases

The water phase and the oil phase are each heated separately to a temperature of approximately 50° C. This temperature is chosen as being substantially the minimum at which it can safely be assumed that all the components of the oil phase will be molten. Ceteareth-12 and Ceteareth-20 have solidification ranges of 34–37° C. and 39–42° C., respectively, and the three oils are all liquid at 25° C. It will be understood that if any of the components of the oil phase had a higher temperature than those just indicated it might be necessary to heat the phases to more than 50° C. and, conversely, that if none of the components of the oil phase had a melting point as high as any of those mentioned above it might not be necessary to heat the phases to a temperature as high as 50° C. Indeed, provided the temperature of the oil phase is sufficiently high that the oil phase and water phase once mixed (see Step 3 below) are at a high enough temperature, and can still form an emulsion, the water phase need not be heated above ambient temperature at all.

During heating, low intensity stirring is carried out, for example, using a propeller or other style blade mixer. This ensures for both phases that heating is substantially uniform and, in the case of the oil phase, it serves to blend the various components together.

Step 3: Emulsifying

The oil phase and water phase are mixed with one another, whilst simultaneously applying stirring. This is carried out whilst maintaining the temperature of the mixture at 50° C. Normally the oil phase would be added to the water phase, which is standard practice for forming oil-in-water emulsions, rather than vice versa. The stirring can be carried out by a blade-type mixer, and while the addition of one phase to the other is taking place mixing will normally need to be relatively intense. This mixing can also be performed by an in-tank rotor/stator homogenizer, though such intense mixing will not normally be necessary. The rate of addition of the oil phase may need to be adjusted having regard to the intensity of mixing. It has been found that if the oil phase is added too fast an apparently solid oil phase material can form in the container in which mixing is taking place, even though the temperature of the mixture during the mixing process is above the melting points of all of the components. The phenomenon is, however, temporary, and if high intensity stirring is continued, without the addition of further oil, the solid material disappears.

Once all the oil phase has been added stirring is continued, but at a lower intensity, and the temperature of the mixture is allowed to fall until it has reached ambient temperature, say 25° C.

The product of Step 3 is a coarse emulsion, in which the water phase is the continuous phase and the oil phase is in the form of droplets, i.e. it is the discontinuous phase. (These are referred to variously herein as droplets and particles, and no distinction is intended to be implied by the use of the different terms). The oil droplets vary greatly in size from some which are of a sub-micrometer in diameter to others which may be as much as a 100 micrometers in diameter, or even more.

Figure 2:
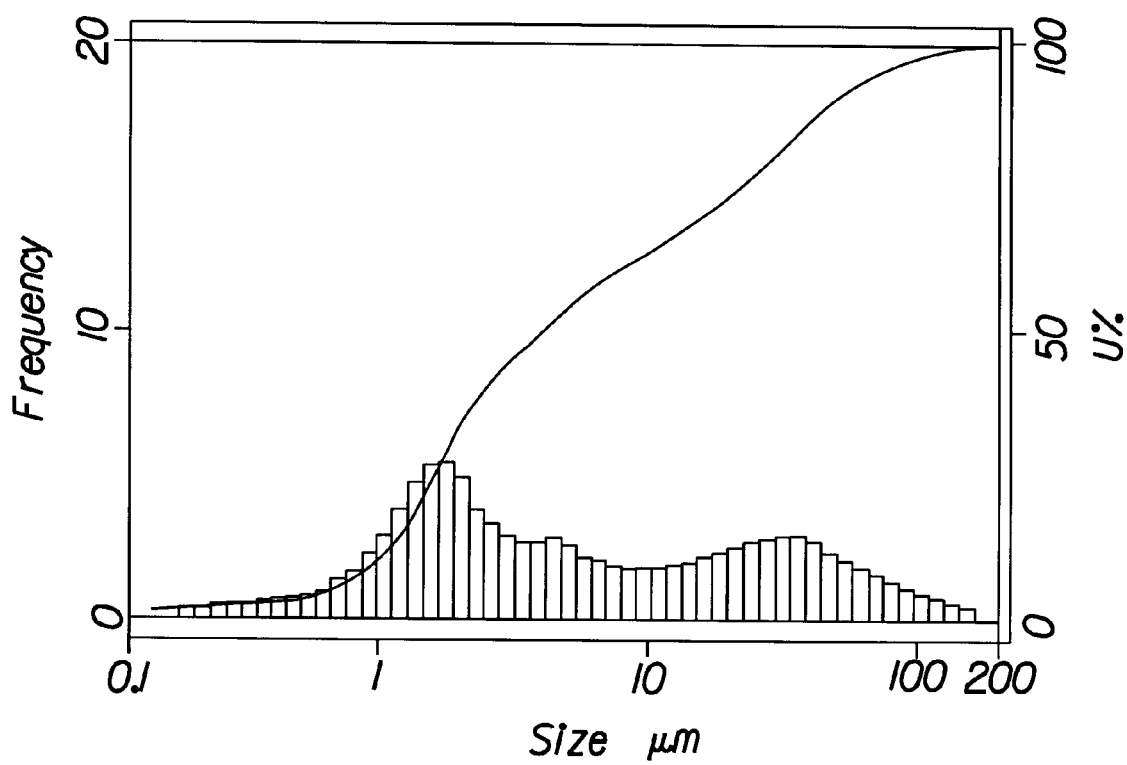
FIGS. 2 to 6 are graphs showing the particle size distribution for various emulsions.

The particle size distribution by volume of one such coarse emulsion was measured using a Horiba LA-500 Particle Size Analyzer available from Horiba Ltd of Miyanohigashi, Kisshoin, Minami-ku, Kyota, Japan, and the results are shown in FIG. 2 and set out in Table 1 below. The median particle size by volume was 3.90 $\mu$m. The percentage of particle volume in the form of particles less than 5.0 $\mu$m in diameter was 54.8%. The standard deviation of the particle size was 20.36 $\mu$m. The upper quartile value was 22.80 $\mu$m, giving an interquartile range of 21.07 $\mu$m. As used herein, the term "median particle size by volume" means that 50% of the total volume of particles consists of particles having an effective diameter greater than the given value, and 50% consists of particles having an effective diameter greater than the given value. The effective diameter of a particle is that which a particle would have if it had the volume which it does in fact have, but was preferably spherical. 5 It should be mentioned at this point that the actual particle sizes are believed to be significantly smaller than the sizes measured by the LA-500, possibly as a result of the fact that the LA-500 is not capable of accurately measuring very small particle sizes. As far as absolute particle sizes are concerned, at least as regards the very small particle sizes with which we are concerned in our homogenized emulsion, more accurate results are believed to be obtainable from another particle size analyzer available from the same company, the LA-910. Some results obtained from the LA-910 are reported later in the specification. Nevertheless, the results obtained from the LA-500 are believed to be valid at least in so far as they give a comparison of particle sizes existing under various circumstances, and it is for that purpose that they are set out in Tables 1 to 5 herein.

TABLE 1

| SEG # | SIZE (microns) | INTVL % | UNDER SIZE % |
|---|---|---|---|
| (01) | 200.0 | 0.0 | 100.0 |
| (02) | 174.6 | 0.2 | 100.0 |
| (03) | 152.4 | 0.4 | 99.8 |
| (04) | 133.1 | 0.6 | 99.4 |
| (05) | 116.2 | 0.7 | 98.9 |
| (06) | 101.4 | 0.9 | 98.1 |
| (07) | 88.58 | 1.1 | 97.2 |
| (08) | 77.34 | 1.4 | 96.0 |
| (09) | 67.52 | 1.7 | 94.7 |
| (10) | 58.95 | 2.0 | 93.0 |
| (11) | 51.47 | 2.3 | 91.1 |
| (12) | 44.94 | 2.5 | 88.8 |
| (13) | 39.23 | 2.7 | 86.3 |
| (14) | 34.25 | 2.8 | 83.5 |
| (15) | 29.91 | 2.7 | 80.7 |
| (16) | 26.11 | 2.8 | 78.0 |
| (17) | 22.80 | 2.3 | 75.5 |
| (18) | 19.90 | 2.2 | 73.1 |
| (19) | 17.38 | 2.0 | 70.9 |
| (20) | 15.17 | 1.8 | 69.0 |
| (21) | 13.25 | 1.7 | 67.1 |
| (22) | 11.56 | 1.6 | 65.5 |
| (23) | 10.10 | 1.6 | 63.8 |
| (24) | 8.82 | 1.6 | 62.2 |
| (25) | 7.70 | 1.7 | 60.7 |
| (26) | 6.72 | 1.8 | 59.0 |
| (27) | 5.87 | 2.0 | 57.2 |
| (28) | 5.12 | 2.4 | 55.2 |
| (29) | 4.47 | 2.6 | 52.9 |
| (30) | 3.90 | 2.5 | 50.3 |
| (31) | 3.41 | 2.5 | 47.7 |
| (32) | 2.98 | 2.6 | 45.2 |
| (33) | 2.60 | 3.1 | 42.6 |
| (34) | 2.27 | 3.7 | 39.5 |
| (35) | 1.98 | 4.8 | 35.8 |
| (36) | 1.73 | 5.4 | 31.0 |
| (37) | 1.51 | 5.3 | 25.7 |
| (38) | 1.32 | 4.6 | 20.4 |
| (39) | 1.15 | 3.7 | 16.8 |
| (40) | 1.00 | 2.8 | 12.1 |
| (41) | 0.88 | 2.0 | 9.3 |
| (42) | 0.77 | 1.5 | 7.3 |
| (43) | 0.67 | 1.0 | 5.8 |
| (44) | 0.58 | 0.8 | 4.8 |
| (45) | 0.51 | 0.6 | 4.0 |
| (46) | 0.45 | 0.5 | 3.4 |
| (47) | 0.39 | 0.5 | 2.9 |
| (48) | 0.34 | 0.4 | 2.4 |
| (49) | 0.30 | 0.4 | 2.0 |
| (50) | 0.26 | 0.4 | 1.6 |
| (51) | 0.23 | 0.3 | 1.2 |
| (52) | 0.20 | 0.3 | 0.9 |
| (53) | 0.17 | 0.3 | 0.6 |
| (54) | 0.15 | 0.2 | 0.3 |
| (55) | 0.13 | 0.1 | 0.1 |
| (56) | 0.11 | 0.0 | 0.0 |

FIG. 7 is a photomicrograph of the coarse emulsion, in which large particles as much as 40 μm are visible.

The stability of this coarse emulsion is relatively low. Left to itself for a short period of time creaming will rapidly begin to occur, that is to say, the oil droplets, which have a density less than that of water, will tend to move upwards in the mixture, and will begin to coalesce with one another. The stability could be improved by, for example, using an in-tank rotor-stator homogenizer, as this will generate smaller particles than the blade mixer. However, this is not necessary, as the relatively low stability of the coarse emulsion is of little consequence for the purposes of the process described here, since the coarse emulsion is not stored but is rapidly passed to the next step in the process, in the course of which, as is described below, a very much higher stability is achieved.

It will be noted that the emulsion produced by Step 3 comprises 12 parts of the water phase to 6 parts of the oil phase, i.e. a ratio of 2:1. As will be explained in the subsequent discussion below, other ratios may be used, though a ratio of 2:1 has been found to be particularly suitable.

The lotion which finally results at the end of the process contains a further 82 parts of water or water-soluble substances, to bring the total up to 100 parts. Thus, in the final product, the oil is diluted, so to speak, by 94 parts of water, whereas at the end of Step 3 the oil in the coarse emulsion is diluted by only 12 parts of water. To put the matter another way, the coarse emulsion can be regarded as being concentrated, compared to the eventual product, by a factor of 94/12 equals 7.83 (approximately 8). This is referred to below as 8× concentration. The use of various concentrations is discussed below.

Step 4: Homogenizing

The coarse emulsion is transformed into a fine emulsion by passing it from a first tank (which may be the one in which the coarse emulsion was formed, or may be different), through a homogenizer into a second tank. While this step is being carried out the coarse emulsion in the first tank continues to be stirred in order to prevent creaming. Stirring may also be applied to the second tank. Passing the emulsion through the homogenizer will generally cause its temperature to increase, typically by about 10_C, and although the application of stirring to the second tank is optional it does have the benefit of ensuring uniform cooling.

The homogenizer used in Step 4 is preferably a high pressure homogenizer. One type of high pressure homogenizer which has been found to work successfully is that available from APV Gaulin GmbH of D-23519 Lübeck, Germany (the Gaulin homogenizer). In the Gaulin homogenizer, the liquid to be homogenized is forced under high pressure, produced by a piston pump arrangement, through a narrow gap, where a pressure drop to less than 1 bar occurs, causing shearing action and cavitation/bubbles. On the downstream side of the gap there is a surface which the liquid strikes, at typical speeds of 300 m/s, causing the particles to break up by impact and implosion of the bubbles.

The above homogenizer has been used in the process at pressures from 350 bar to 700 bar. The homogenization achieved at the higher pressure was not perceptibly better than that achieved at the lower pressure, and it is reasonable to infer, therefore, that acceptable homogenization could be achieved at pressures below 350 bar.

Another type of high pressure homogenizer which has been successfully used in the present invention is that available from Microfluidics International Corporation, 30 Ossipee Road, Newton, Mass. 02164-9101, USA. This has been successfully used at pressures of 175 bar, 350 bar and 700 bar, though there is reason to believe that pressures higher or lower than this could also be used. This homogenizer uses an interaction chamber in which two high pressure streams interact at high velocities in microchannels. Shear, impact and cavitation forces act on the liquid to achieve particle size reduction.

It is to be understood that although the foregoing description of the operation of these homogenizers is given to the best of our knowledge and belief, we cannot warrant that the details thereof are correct. Suffice it to say, however, that the types of homogenizer identified above can be used successfully in the process of the present invention.

The size of the oil phase droplets in the homogenized product produced in Step 4 is much reduced compared to the size of the droplets in the coarse emulsion. Typically the median particle size is less than 1 μm. Furthermore, the spread of particle sizes is much narrower than it is in the coarse emulsion, with a very small percentage of the particles, if any, having a size greater than a few micrometers. FIG. 8 is a photomicrograph of such a homogenized emulsion, and no large particles are visible. This emulsion was produced by passing a coarse emulsion once through a Gaulin homogenizer at 350 bar at ambient temperature (25° C.).

Figure 3:
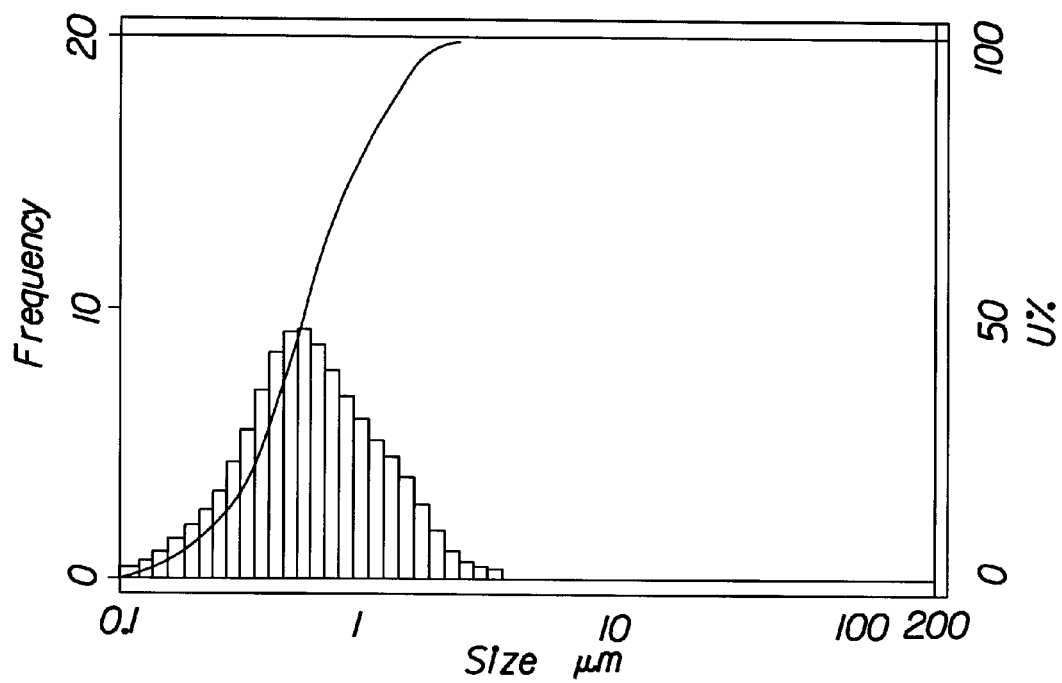

The particle size distribution by volume of one such homogenized emulsion, produced using a Gaulin Lab 40 homogenizer, under a pressure of 350 bar, was measured by the LA-500 analyzer identified above, and the results are shown in FIG. 3 and set out in Table 2 below. Homogenization was carried out at 25° C. The median particle size was 0.58 μm. The percentage of particle volume in the form of particles less than 5.0 μm in diameter was 100%, and indeed almost no particles larger than 3 μm were observed. The standard deviation of the particle size was 0.39 μm. The upper quartile value was 0.88 μm and the lower quartile value was 0.405 μm, giving an interquartile range of 0.475 μm.

TABLE 2

| SEG # | SIZE (microns) | INTVL % | UNDER SIZE % |
|---|---|---|---|
| (01) | 200.0 | 0.0 | 100.0 |
| (02) | 174.6 | 0.0 | 100.0 |
| (03) | 152.4 | 0.0 | 100.0 |
| (04) | 133.1 | 0.0 | 100.0 |
| (05) | 116.2 | 0.0 | 100.0 |
| (06) | 101.4 | 0.0 | 100.0 |
| (07) | 88.58 | 0.0 | 100.0 |
| (08) | 77.34 | 0.0 | 100.0 |
| (09) | 67.52 | 0.0 | 100.0 |
| (10) | 58.95 | 0.0 | 100.0 |
| (11) | 51.47 | 0.0 | 100.0 |
| (12) | 44.94 | 0.0 | 100.0 |
| (13) | 39.23 | 0.0 | 100.0 |
| (14) | 34.25 | 0.0 | 100.0 |
| (15) | 29.91 | 0.0 | 100.0 |
| (16) | 26.11 | 0.0 | 100.0 |
| (17) | 22.80 | 0.0 | 100.0 |
| (18) | 19.90 | 0.0 | 100.0 |
| (19) | 17.38 | 0.0 | 100.0 |
| (20) | 15.17 | 0.0 | 100.0 |
| (21) | 13.25 | 0.0 | 100.0 |
| (22) | 11.56 | 0.0 | 100.0 |
| (23) | 10.10 | 0.0 | 100.0 |
| (24) | 8.82 | 0.0 | 100.0 |
| (25) | 7.70 | 0.0 | 100.0 |
| (26) | 6.72 | 0.0 | 100.0 |
| (27) | 5.87 | 0.0 | 100.0 |
| (28) | 5.12 | 0.0 | 100.0 |
| (29) | 4.47 | 0.0 | 100.0 |
| (30) | 3.90 | 0.0 | 100.0 |
| (31) | 3.41 | 0.1 | 100.0 |
| (32) | 2.98 | 0.2 | 99.0 |
| (33) | 2.60 | 0.4 | 99.6 |
| (34) | 2.27 | 0.8 | 99.2 |
| (35) | 1.98 | 1.6 | 98.6 |
| (36) | 1.73 | 2.6 | 96.9 |
| (37) | 1.51 | 3.6 | 94.2 |
| (38) | 1.32 | 4.3 | 90.6 |
| (39) | 1.15 | 4.9 | 86.3 |

TABLE 2-continued

| SEG # | SIZE (microns) | INTVL % | UNDER SIZE % |
|---|---|---|---|
| (40) | 1.00 | 5.6 | 81.4 |
| (41) | 0.88 | 6.5 | 75.8 |
| (42) | 0.77 | 7.5 | 69.2 |
| (43) | 0.67 | 8.5 | 61.7 |
| (44) | 0.58 | 9.1 | 53.2 |
| (45) | 0.51 | 9.1 | 44.1 |
| (46) | 0.45 | 8.2 | 35.1 |
| (47) | 0.39 | 6.8 | 26.9 |
| (48) | 0.34 | 5.4 | 20.1 |
| (49) | 0.30 | 4.1 | 14.7 |
| (50) | 0.26 | 3.2 | 10.5 |
| (51) | 0.23 | 2.4 | 7.4 |
| (52) | 0.20 | 1.8 | 4.9 |
| (53) | 0.17 | 1.3 | 3.1 |
| (54) | 0.15 | 0.9 | 1.8 |
| (55) | 0.13 | 0.6 | 0.8 |
| (56) | 0.11 | 0.3 | 0.3 |

Figure 10:
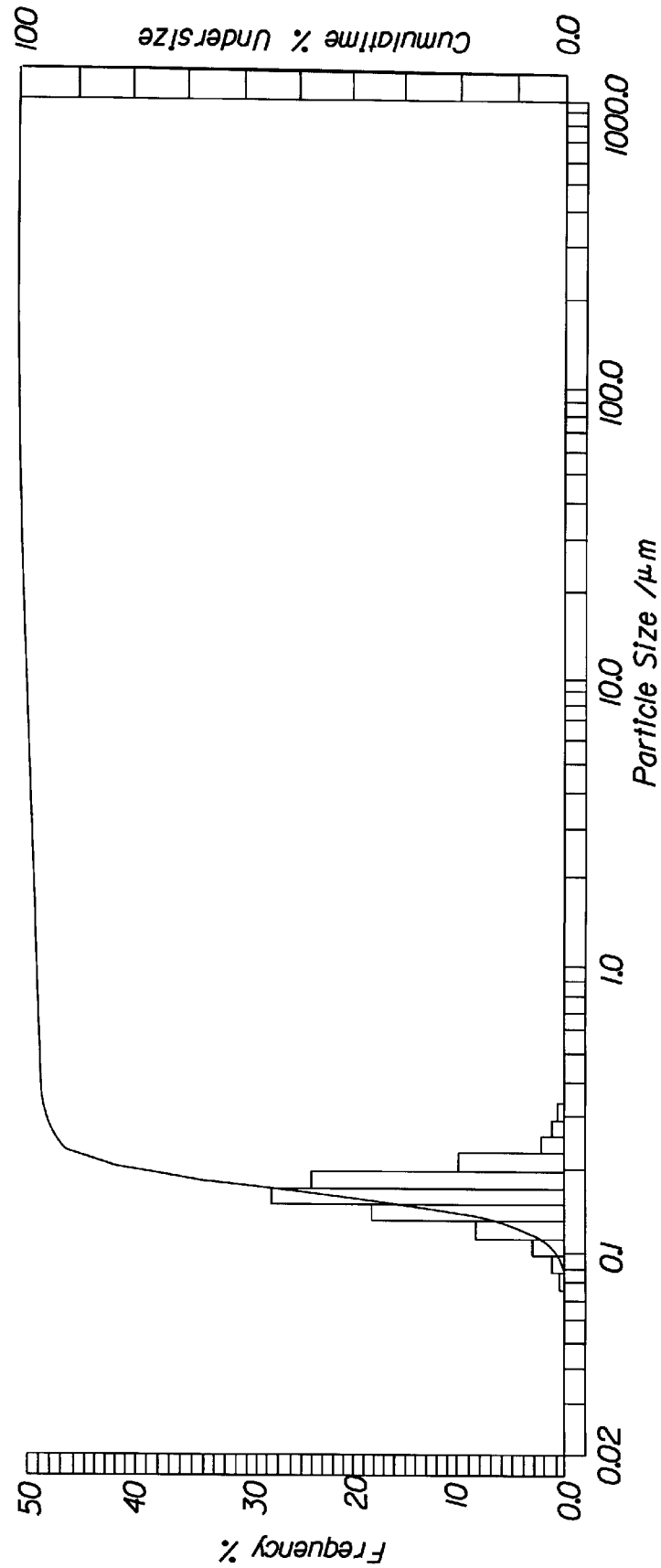
FIG. 10 is a graph for the same emulsion as that to which FIG. 4 relates, but measured using different equipment.

As already mentioned, it is believed that the absolute particle size is more accurately given by measurements obtained on an LA-910 analyzer, and Table 6 below gives results corresponding to those of Table 3, but obtained with an LA-910. The corresponding graph is given as FIG. 10. From Table 6, the median particle size can be determined as being 0.164 μm, and the standard deviation of the particle size as 0.087 μm. No particle sizes greater than 1.151 μm are detected.

TABLE 6

| SIZE (μm) | INTVL % | UNDER Size % |
|---|---|---|
| 1.318 | 0.00 | 100.00 |
| 1.151 | 0.15 | 100.00 |
| 1.005 | 0.23 | 99.85 |
| 0.877 | 0.31 | 99.62 |
| 0.766 | 0.32 | 99.31 |
| 0.669 | 0.29 | 98.99 |
| 0.584 | 0.25 | 98.70 |
| 0.510 | 0.24 | 98.45 |
| 0.445 | 0.23 | 98.21 |
| 0.389 | 0.35 | 97.98 |
| 0.339 | 0.68 | 97.63 |
| 0.296 | 1.20 | 96.95 |
| 0.259 | 2.52 | 95.75 |
| 0.226 | 10.13 | 93.23 |
| 0.197 | 23.80 | 83.09 |
| 0.172 | 27.83 | 59.29 |
| 0.150 | 18.24 | 31.45 |
| 0.131 | 8.61 | 13.22 |
| 0.115 | 3.09 | 4.71 |
| 0.100 | 1.13 | 1.63 |
| 0.087 | 0.49 | 0.49 |
| 0.075 | 0.00 | 0.00 |
| 0.067 | 0.00 | 0.00 |
| 0.058 | 0.00 | 0.00 |
| 0.051 | 0.00 | 0.00 |
| 0.044 | 0.00 | 0.00 |
| 0.039 | 0.00 | 0.00 |
| 0.034 | 0.00 | 0.00 |
| 0.029 | 0.00 | 0.00 |
| 0.026 | 0.00 | 0.00 |
| 0.022 | 0.00 | 0.00 |

Figure 4:
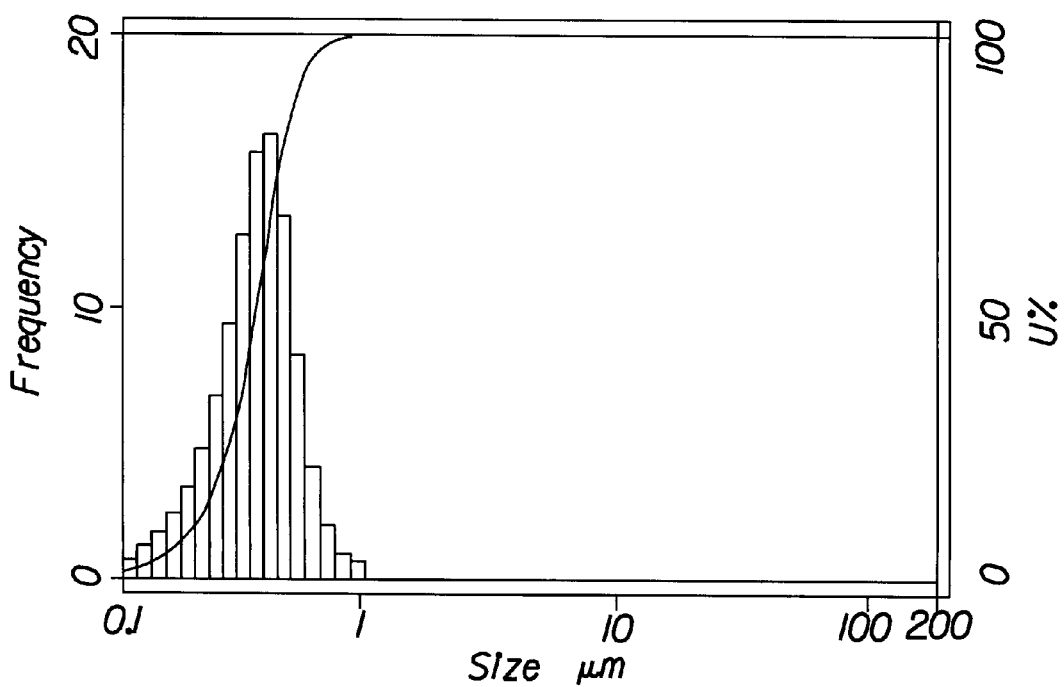

The median particle size, and the particle size distribution, can be further reduced by subjecting the homogenized emulsion to more than one pass through the homogenizer. The results of subjecting the emulsion described above with reference to FIG. 3 and Table 2 to a second pass through the same homogenizer under the same conditions are shown in FIG. 4 and Table 3.

TABLE 3

| SEG # | SIZE (microns) | INTVL % | UNDER SIZE % |
|---|---|---|---|
| (01) | 200.0 | 0.0 | 100.0 |
| (02) | 174.6 | 0.0 | 100.0 |
| (03) | 152.4 | 0.0 | 100.0 |
| (04) | 133.1 | 0.0 | 100.0 |
| (05) | 116.2 | 0.0 | 100.0 |
| (06) | 101.4 | 0.0 | 100.0 |
| (07) | 88.58 | 0.0 | 100.0 |
| (08) | 77.34 | 0.0 | 100.0 |
| (09) | 67.52 | 0.0 | 100.0 |
| (10) | 58.95 | 0.0 | 100.0 |
| (11) | 51.47 | 0.0 | 100.0 |
| (12) | 44.94 | 0.0 | 100.0 |
| (13) | 39.23 | 0.0 | 100.0 |
| (14) | 34.25 | 0.0 | 100.0 |
| (15) | 29.91 | 0.0 | 100.0 |
| (16) | 26.11 | 0.0 | 100.0 |
| (17) | 22.80 | 0.0 | 100.0 |
| (18) | 19.90 | 0.0 | 100.0 |
| (19) | 17.38 | 0.0 | 100.0 |
| (20) | 15.17 | 0.0 | 100.0 |
| (21) | 13.25 | 0.0 | 100.0 |
| (22) | 11.56 | 0.0 | 100.0 |
| (23) | 10.10 | 0.0 | 100.0 |
| (24) | 8.82 | 0.0 | 100.0 |
| (25) | 7.70 | 0.0 | 100.0 |
| (26) | 6.72 | 0.0 | 100.0 |
| (27) | 5.87 | 0.0 | 100.0 |
| (28) | 5.12 | 0.0 | 100.0 |
| (29) | 4.47 | 0.0 | 100.0 |
| (30) | 3.90 | 0.0 | 100.0 |
| (31) | 3.41 | 0.0 | 100.0 |
| (32) | 2.98 | 0.0 | 100.0 |
| (33) | 2.60 | 0.0 | 100.0 |
| (34) | 2.27 | 0.0 | 100.0 |
| (35) | 1.98 | 0.0 | 100.0 |
| (36) | 1.73 | 0.0 | 100.0 |
| (37) | 1.51 | 0.0 | 100.0 |
| (38) | 1.32 | 0.0 | 100.0 |
| (39) | 1.15 | 0.0 | 100.0 |
| (40) | 1.00 | 0.2 | 100.0 |
| (41) | 0.88 | 0.5 | 99.8 |
| (42) | 0.77 | 1.5 | 99.3 |
| (43) | 0.67 | 3.8 | 97.9 |
| (44) | 0.58 | 8.1 | 94.1 |
| (45) | 0.51 | 13.3 | 86.0 |
| (46) | 0.45 | 16.3 | 72.7 |
| (47) | 0.39 | 15.7 | 56.3 |
| (48) | 0.34 | 12.6 | 40.7 |
| (49) | 0.30 | 9.2 | 28.1 |
| (50) | 0.26 | 6.5 | 18.9 |
| (51) | 0.23 | 4.4 | 12.4 |
| (52) | 0.20 | 3.1 | 7.9 |
| (53) | 0.17 | 2.2 | 4.8 |
| (54) | 0.15 | 1.4 | 2.6 |
| (55) | 0.13 | 0.8 | 1.2 |
| (56) | 0.11 | 0.4 | 0.4 |

The median particle size of this homogenized emulsion was 0.39 μm, a reduction of over 30% compared to a value of 0.58 μm for the same embodiment after one pass through the homogenizer. No particle larger than 1 μm was observed. The standard deviation of the particle size was 0.13 μm. The upper quartile value was 0.51 μm and the lower quartile value was 0.30 μm, giving an interquartile range of 0.19 μm.

Figure 5:
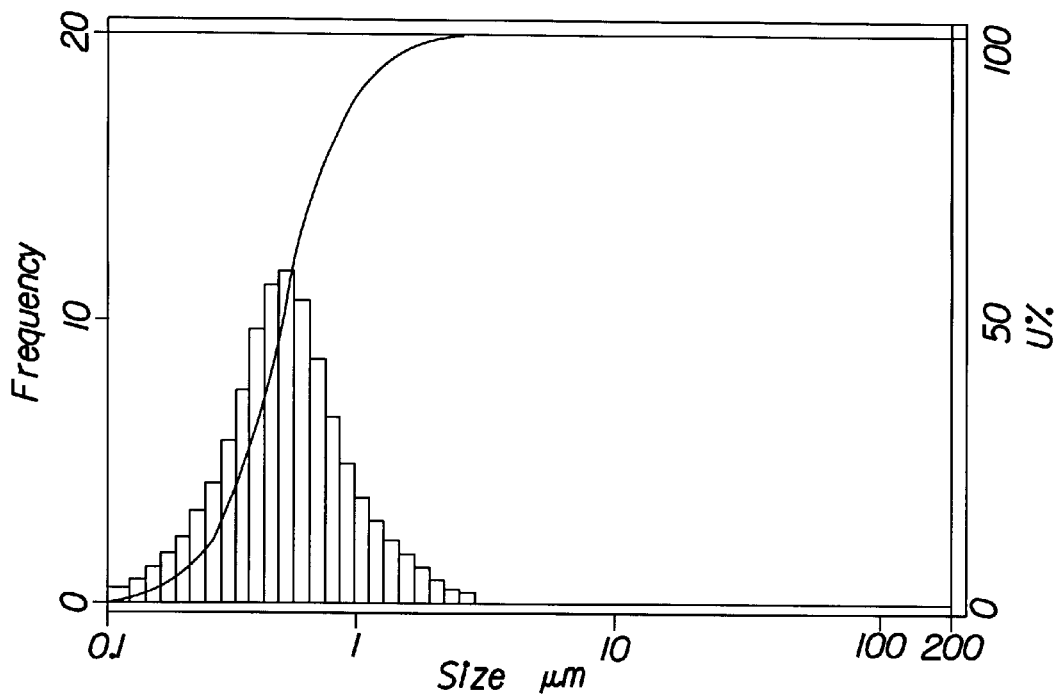
Figure 6:
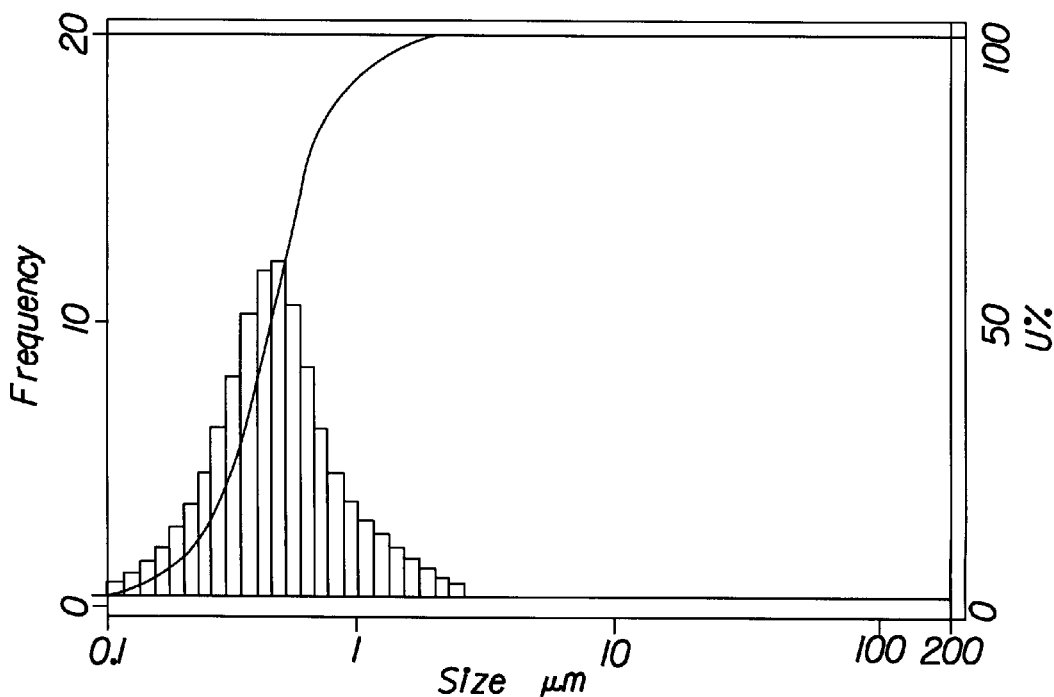

The possible effects of temperature on the homogenization process were investigated by repeating the process represented by FIG. 3 (Table 2) and FIG. 4 (Table 3) under a temperature of 50_C, but with the other conditions remaining unaltered. The results are shown in FIG. 5 and Table 4 for the first pass, and FIG. 6 and Table 5 for the second pass.

TABLE 4

| SEG # | SIZE (microns) | INTVL % | UNDER SIZE % |
|---|---|---|---|
| (01) | 200.0 | 0.0 | 100.0 |
| (02) | 174.6 | 0.0 | 100.0 |
| (03) | 152.4 | 0.0 | 100.0 |
| (04) | 133.1 | 0.0 | 100.0 |
| (05) | 116.2 | 0.0 | 100.0 |
| (06) | 101.4 | 0.0 | 100.0 |
| (07) | 88.58 | 0.0 | 100.0 |
| (08) | 77.34 | 0.0 | 100.0 |
| (09) | 67.52 | 0.0 | 100.0 |
| (10) | 58.95 | 0.0 | 100.0 |
| (11) | 51.47 | 0.0 | 100.0 |
| (12) | 44.94 | 0.0 | 100.0 |
| (13) | 39.23 | 0.0 | 100.0 |
| (14) | 34.25 | 0.0 | 100.0 |
| (15) | 29.91 | 0.0 | 100.0 |
| (16) | 26.11 | 0.0 | 100.0 |
| (17) | 22.80 | 0.0 | 100.0 |
| (18) | 19.90 | 0.0 | 100.0 |
| (19) | 17.38 | 0.0 | 100.0 |
| (20) | 15.17 | 0.0 | 100.0 |
| (21) | 13.25 | 0.0 | 100.0 |
| (22) | 11.56 | 0.0 | 100.0 |
| (23) | 10.10 | 0.0 | 100.0 |
| (24) | 8.82 | 0.0 | 100.0 |
| (25) | 7.70 | 0.0 | 100.0 |
| (26) | 6.72 | 0.0 | 100.0 |
| (27) | 5.87 | 0.0 | 100.0 |
| (28) | 5.12 | 0.0 | 100.0 |
| (29) | 4.47 | 0.0 | 100.0 |
| (30) | 3.90 | 0.0 | 100.0 |
| (31) | 3.41 | 0.0 | 100.0 |
| (32) | 2.98 | 0.0 | 100.0 |
| (33) | 2.60 | 0.1 | 100.0 |
| (34) | 2.27 | 0.2 | 99.0 |
| (35) | 1.98 | 0.5 | 99.6 |
| (36) | 1.73 | 1.0 | 99.1 |
| (37) | 1.51 | 1.5 | 98.1 |
| (38) | 1.32 | 2.1 | 96.6 |
| (39) | 1.15 | 2.7 | 94.5 |
| (40) | 1.00 | 3.5 | 91.9 |
| (41) | 0.88 | 4.7 | 98.4 |
| (42) | 0.77 | 6.4 | 83.7 |
| (43) | 0.67 | 8.5 | 77.3 |
| (44) | 0.58 | 10.5 | 68.8 |
| (45) | 0.51 | 11.6 | 58.3 |
| (46) | 0.45 | 11.2 | 46.6 |
| (47) | 0.39 | 9.5 | 35.4 |
| (48) | 0.34 | 7.4 | 25.9 |
| (49) | 0.30 | 5.5 | 18.5 |
| (50) | 0.26 | 4.1 | 13.0 |
| (51) | 0.23 | 3.0 | 8.9 |
| (52) | 0.20 | 2.2 | 5.9 |
| (53) | 0.17 | 1.6 | 3.7 |
| (54) | 0.15 | 1.1 | 2.1 |
| (55) | 0.13 | 0.7 | 1.0 |
| (56) | 0.11 | 0.3 | 0.3 |

TABLE 5

| SEG # | SIZE (microns) | INTVL % | UNDER SIZE % |
|---|---|---|---|
| (01) | 200.0 | 0.0 | 100.0 |
| (02) | 174.6 | 0.0 | 100.0 |
| (03) | 152.4 | 0.0 | 100.0 |
| (04) | 133.1 | 0.0 | 100.0 |
| (05) | 116.2 | 0.0 | 100.0 |
| (06) | 101.4 | 0.0 | 100.0 |
| (07) | 88.58 | 0.0 | 100.0 |
| (08) | 77.34 | 0.0 | 100.0 |
| (09) | 67.52 | 0.0 | 100.0 |
| (10) | 58.95 | 0.0 | 100.0 |
| (11) | 51.47 | 0.0 | 100.0 |

TABLE 5-continued

| SEG # | SIZE (microns) | INTVL % | UNDER SIZE % |
|---|---|---|---|
| (12) | 44.94 | 0.0 | 100.0 |
| (13) | 39.23 | 0.0 | 100.0 |
| (14) | 34.25 | 0.0 | 100.0 |
| (15) | 29.91 | 0.0 | 100.0 |
| (16) | 26.11 | 0.0 | 100.0 |
| (17) | 22.80 | 0.0 | 100.0 |
| (18) | 19.90 | 0.0 | 100.0 |
| (19) | 17.38 | 0.0 | 100.0 |
| (20) | 15.17 | 0.0 | 100.0 |
| (21) | 13.25 | 0.0 | 100.0 |
| (22) | 11.56 | 0.0 | 100.0 |
| (23) | 10.10 | 0.0 | 100.0 |
| (24) | 8.82 | 0.0 | 100.0 |
| (25) | 7.70 | 0.0 | 100.0 |
| (26) | 6.72 | 0.0 | 100.0 |
| (27) | 5.87 | 0.0 | 100.0 |
| (28) | 5.12 | 0.0 | 100.0 |
| (29) | 4.47 | 0.0 | 100.0 |
| (30) | 3.90 | 0.0 | 100.0 |
| (31) | 3.41 | 0.0 | 100.0 |
| (32) | 2.98 | 0.0 | 100.0 |
| (33) | 2.60 | 0.2 | 100.0 |
| (34) | 2.27 | 0.3 | 99.8 |
| (35) | 1.98 | 0.7 | 99.5 |
| (36) | 1.73 | 1.1 | 98.8 |
| (37) | 1.51 | 1.6 | 97.7 |
| (38) | 1.32 | 1.9 | 96.1 |
| (39) | 1.15 | 2.4 | 94.2 |
| (40) | 1.00 | 3.1 | 91.8 |
| (41) | 0.88 | 4.2 | 88.7 |
| (42) | 0.77 | 5.8 | 84.4 |
| (43) | 0.67 | 7.9 | 78.6 |
| (44) | 0.58 | 10.2 | 70.7 |
| (45) | 0.51 | 11.7 | 60.5 |
| (46) | 0.45 | 11.5 | 48.8 |
| (47) | 0.39 | 9.9 | 37.3 |
| (48) | 0.34 | 7.8 | 27.3 |
| (49) | 0.30 | 5.9 | 19.5 |
| (50) | 0.26 | 4.3 | 13.7 |
| (51) | 0.23 | 3.2 | 9.3 |
| (52) | 0.20 | 2.3 | 6.1 |
| (53) | 0.17 | 1.7 | 3.8 |
| (54) | 0.15 | 1.1 | 2.2 |
| (55) | 0.13 | 0.7 | 1.0 |
| (56) | 0.11 | 0.3 | 0.3 |

The median particle size after the first pass was 0.51 μm, a slight reduction on the value of 0.58 μm obtained at 25° C. However the second pass at 50° C. had no perceptible effect on reducing the median particle size further, also giving a value of 0.51 μm. Furthermore, unlike the situation at 25° C., the second pass had no measurable effect in reducing the maximum particle size. Accordingly, it appears that although the use of a higher temperature may be advantageous if it desired to carry out homogenization using only a single pass, much better results can be obtained by using a plurality of passes at a lower temperature.

For the record it is noted that after the first pass the standard deviation of the particle size was 0.295 μm. The upper quartile value was 0.67 μm and the lower quartile value was 0.34 μm, giving an interquartile range of 0.33 μm. After the second pass the standard deviation of the particle size was 0.29 μm. The upper quartile value was 0.67 μm and the lower quartile value was 0.34 μm, giving an interquartile range of 0.33 μm.

It is also possible to operate Step 4 by continually recycling the output of the homogenizer to the tank which is connected to the input of the homogenizer. However, this has the disadvantage that some portions of the coarse emulsion may pass through the homogenizer several times, whereas other portions may remain in the tank and never pass through the homogenizer. Accordingly, this mode of operating is less desirable from the point of view of avoiding the possibility that at least some large particles will remain and not be broken down into smaller particles.

Step 5: Dilution

An aqueous dilution agent is prepared, for example according to the following composition:

Purified water (80.1 parts)
Phenoxyethanol (0.9 parts)
Sodium Benzoate (0.4 parts)
Tetrasodium EDTA (0.1 parts)

Phenoxyethanol is a liquid which is water-soluble (at least at this concentration), and the last two mentioned in this list are water-soluble solids. All three are stirred into the purified water to form an aqueous solution. They form part of a preservative system which is incorporated in the product to prevent the growth of bacteria and other undesired organisms. The remaining components of the preservative system are incorporated in Step 6 below, for reasons which are explained in relation to that step.

The homogenized emulsion produced in Step 4 is added to the dilution agent described above at room temperature, with simultaneous stirring. The stirring has the effect of ensuring that any clusters of the droplets are broken up and dispersed throughout the dilution agent. It is found that relatively little energy is required to effect this, and the stirring does not therefore need to be vigorous. A blade type stirrer has been found to be adequate for the purpose, though an alternative type, for example a static mixer, though which the contents of the tank are passed, might be used instead.

Rather than adding the emulsion to the dilution agent one could add the dilution agent to the emulsion, and, at least in theory, it might be considered preferable to do this from the point of view of the properties of the product being made. This is because in this way the emulsion is progressively diluted, rather than being suddenly diluted when the first drops of emulsion enter dilution agent. There is, at least in theory, a risk that sudden dilution will deplete the oil droplets of surfactant. In practice, however, provided dilution is not carried out over too long a period, this problem is found to be of no practical consequence. In any event, adding dilution agent to emulsion is disadvantageous from a manufacturing point of view, since it requires the concentrated emulsion to be held for the purpose in a vessel having a volume very much larger than the volume of the concentrated, coarse emulsion.

Step 6: Formula completion

The following ingredients are added to the composition prepared in Step 5, accompanied by stirring.

Methyl Paraben (0.2 parts)
Propyl Paraben (0.1 parts)
Fragrance (0.1 parts)

The Methyl and Propyl Parabens form the remaining components of the preservative system. Both are very soluble in oil, and have a relatively low solubility in water, and the reason for adding them in Step 6, rather than Step 5 is with a view to trying to ensure that as much as possible of these two components dissolves in the water rather than the oil. The rationale behind adding in Step 6 is that at the start of that step there is over five times as much water present as there is at the start of Step 5, and in so far as the Methyl and Propyl Parabens are partitioned between the water and the oil the proportion which dissolves in the water should be greater if they are added at a point in the process when there is a larger quantity of water present. It should be added that phenoxyethanol, which is added in Step 5, is also soluble to some extent in oil, can be added in Step 5 because its water solubility is much greater than in the case of the parabens.

The reason for endeavouring to ensure that the preservatives dissolve as far as possible in the water phase rather than the oil phase is that the organisms whose growth they are intended to prevent can exist only in the water phase, and the oil phase is inherently sterile.

It will be appreciated that alternative preservative systems can be used to the one described above, and the above described system can be modified as to the quantities of the components which it contains. One such modification which is believed to be feasible is to reduce the amount of phenoxyethanol from 0.9% to 0.7%. Even with this reduction, the effect of the preservative system appears to be satisfactory. However, further reduction to 0.5% phenoxyethanol appears to be unacceptable, and a system with this quantity of phenoxyethanol was found not to have the preferred level of bactericidal action.

Finally, as part of Step 6, citric acid is added to adjust the pH. From the point of view achieving a total formula of 100 parts it has been assumed that the amount of citric acid added amounts to 0.1 parts. However, the amount added in any particular situation is that which is required to achieve a pH of 5.5. Accordingly, what is done is to determine the pH of the composition before the citric acid (it will always be greater than 5.5) and then add just that amount of citric acid which is required to achieve the desired pH.

The lotion thus produced can then be stored, if necessary after allowing it to reach ambient temperature, ready for application to a flexible fibrous substrate to produce the baby wipes. Normally one would expect application to take place within a short period, say a few hours, of the lotion being produced, but it is sufficiently stable to be stored for a much longer period of time, should that be required.

Typically, the substrate material used will be a non-woven web of, for example, a 50:50 blend of viscose and polyethylene terephthalate or polypropylene. This can be applied by any conventional method, for example being forced through apertures in a tube which is in contact with the substrate, while the substrate passes across the tube. Typically application will be carried out on a substrate unwound from a roll having a width equal to a substantial number of the baby wipes which it is intended to produce, and the substrate, with the lotion applied thereto, is then severed to produce the individual wipes. It is to be understood, however, that the above description is given by way of illustration only, and that various conventional processes are available in the art for baby wipe production.

The viscosity of the lotion is very low (typically less than 5 mPa.s) i.e. it behaves substantially like water from this point of view. It is therefore very easy to apply to the substrate material, which is not the case for more viscous materials. Furthermore, the low viscosity is believed to enhance its cleansing ability.

The above description has focused on a process in which a concentrated, coarse emulsion is produced, the coarse emulsion is homogenized, and the homogenized product is then diluted to give the final product. It is to be understood, however, that the dilution step can be omitted if the initial coarse emulsion contains a much larger amount of water, sufficient that no further water need be added after homogenization. The final product obtained in this way is substantially indistinguishable from that obtained by homogenizing the concentrated coarse emulsion and then diluting the homogenized material. However, homogenizing the diluted material, as opposed to the concentrate, greatly increases the amount of energy required, particularly for heating, and is therefore not preferred.

Figure 9:
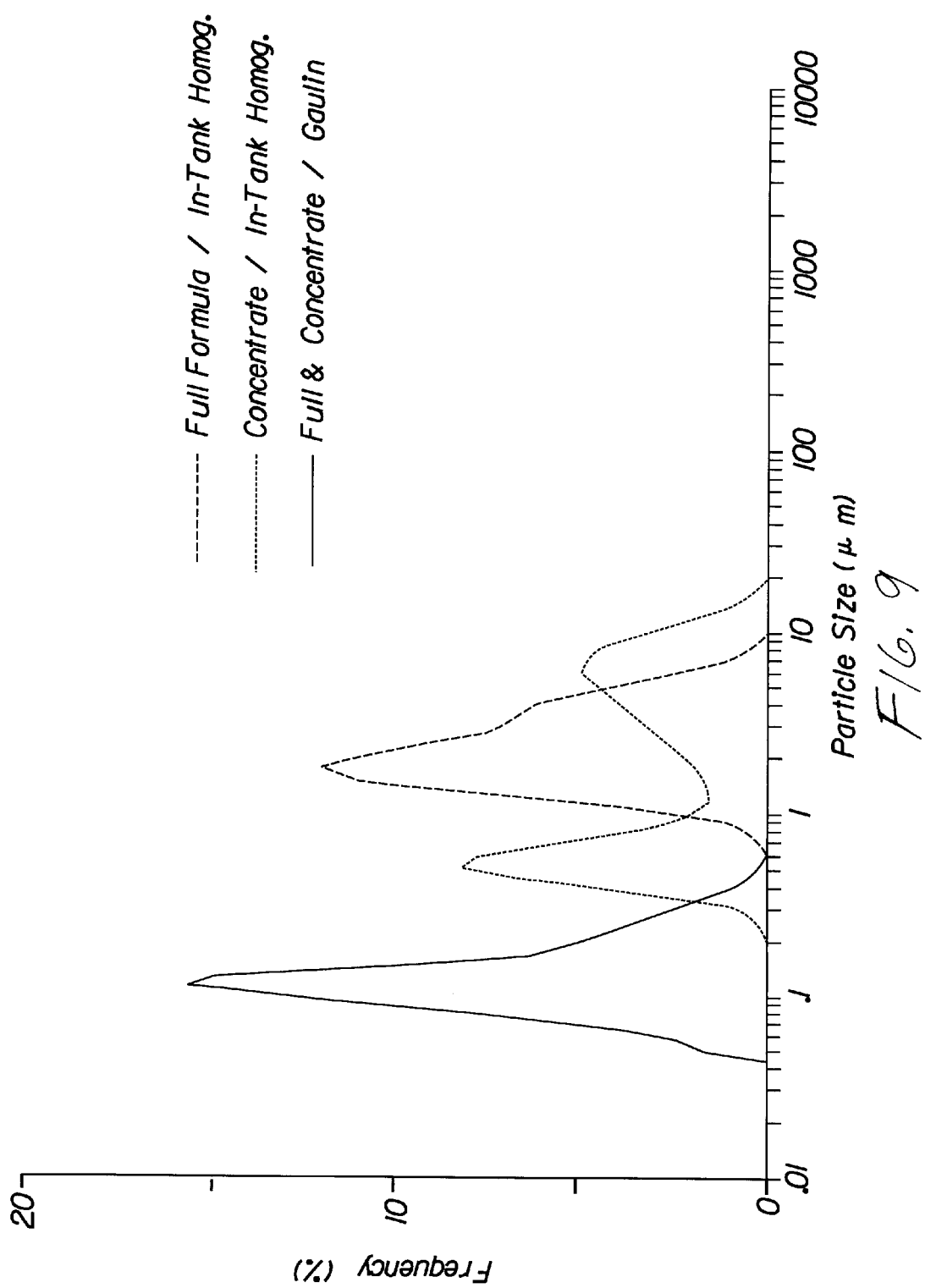
FIG. 9 is a graph which shows, by way of comparison, the particle size distribution of several emulsions.

FIG. 9 of the drawings is a graph on which are plotted typical particle distribution, as measured by a Horiba LA-910 particle size distribution analyzer, for products obtained in a number of different ways. Line 3 is a graph which represents a typical distribution obtained using a Gaulin homogenizer both when it is a concentrated coarse emulsion which is homogenized and then diluted, and when it is an already diluted coarse emulsion which is homogenized. A single line represents both. Line 1 represents the result of carrying out in-tank homogenization of a diluted coarse emulsion, and line 2 represents the result of carrying out the same process on a concentrated coarse emulsion. It will be seen that the median particle size for both lines 1 and 2, and their particle size distributions, are very much greater than is the case with line 3. Lines 1 and 2 represent the result of processes in which the homogenizer is located within a tank containing the emulsion to be homogenized, and the homogenizer has an inlet through which it draws liquid from the tank and an outlet through which it expels liquid into the tank. It will be understood that in such cases it is possible for some parts of the liquid never to pass through the homogenizer, whilst other parts may pass through more than once. In contrast, with a homogenizer such as the Gaulin, which is used in an in-line fashion, all the liquid passes through it once or more than once, depending on whether there is a single pass or more than one pass.

There is set out below a specific example for the carrying out of a method according to the invention.

EXAMPLE (a) Making a Concentrate Batch

The following is a description of the making of a concentrate batch. The concentrate batch size was 10 kg. The following amounts of materials were used:

Oil Phase 1110 g Mineral Oil 555 g Dicaprylyl Ether 555 g Caprylic/Capric Triglycerides 555 g Ceteareth-12

555 g Ceteareth-20

Water Phase 6670 g Water, purified

The oil phase was heated to 50° C. while stirring gently with a blade stirring device to ensure uniform heating. The water phase was heated to 50° C. while stirring gently with a blade stirring device to ensure uniform heating. The oil phase was added to the water phase while stirring rapidly with a blade style stirring device. Then, after the entire oil phase was added, the mixture was stirred gently until it reached 25° C. The emulsified concentrate was the processed through a Gaulin Lab 40 at settings of 315 bar on the primary valve, and 35 bar on the secondary valve, giving a total effective pressure of 350 bar. The concentrate was then passed a second time through the Gaulin at the same settings.

(b) Diluting the Concentrate Batch

The following description is of the dilution of the concentrate to create the final lotion formula. The final lotion batch to be created was 2000 g in size. In this step, a Dilution Water Phase was prepared as follows:

Dilution Water Phase 10.0 g Phenoxyethanol 8.0 g Potassium Sorbate 2.8 g Benzalkonium Chloride (BKC) (50% solution)

2.0 g Tetrasodium EDTA 1.2 g Citric Acid 1614.0 g Water, purified

The components of the dilution water phase were added together and stirred with a blade style mixer until all components were dissolved. The rate of stirring determines how fast components are dissolved.

In the next step, 360 g of the concentrate made as described in (a) above was added into the dilution water phase while continuing to stir with the blade mixer. After the concentrate was added, 0.1 g of a fragrance was added to complete the composition. After all ingredients were added, the lotion was stirred for approximately 10 minutes to ensure uniform dilution of the concentrate, and uniform mixing of the fragrance into the lotion.

It is to be noted that this Example employs a different preservative system to that described earlier in the specification.

Finally, the following tables give some data regarding the stability of emulsions produced according to the invention. The stability was judged according to the following classification system, in which the appearance of the emulsion was allocated to one of seven classes. An emulsion classed as anywhere from 1 to 4 is regarded as completely acceptable, a classification of 6 or 7 is not acceptable, and a classification of 5 is regarded as transitional.

| Stability classification | |
|---|---|
| 1. | stable, homogeneous |
| | no visible oil droplets or transparency |
| 2. | traces of separation |
| | oily droplets on top or noticeable while turning the vessel |
| 3. | slight creaming on top (hardly visible) |
| | aqueous phase milky |
| 4. | creaming on top |
| | aqueous phase slightly transparent |
| | no visible separation of water on the bottom |
| 5. | creaming on top |
| | aqueous phase has no complete, but distinct transparency |
| | no visible separation of water on the bottom |
| 6. | separated into 2 or more phases |
| | separation of water on the bottom <1.0 cm |
| 7. | separated into 2 or more phases |
| | separation of water on the bottom >1.0 cm |

| Stability Data (1) | | | | | | |
|---|---|---|---|---|---|---|
| | Ex. 1 | Ex. 2 | Ex. 3 | Ex. 4 | Ex. 5 | Ex. 6 |
| description of product preservative system | Paraben/sodium benzoate/ Phenoxy 0.9% | Paraben/sodium benzoate/ Phenoxy 0.7% | BKC System | BKC System | Paraben/sodium benzoate/ Phenoxy 0.9% | BKC System |
| process | concentrate | concentrate | concentrate | concentrate | concentrate | concentrate |
| mean particle size [μm] after manufacturing | n.a. | n.a. | n.a. | 0.35 | 0.40 | 0.44 |
| stability 40° C. | | | | | | |
| storage time | 3 months | 3 months | 8 weeks | 8 weeks | 3 months | 10 weeks |
| classification | 3 | 3 | 1 | 3 | 3 | 3–4 |
| specific comments | | | yellowing | yellowing | | yellowing |
| particle size [μm] after storage at 40° C. | n.a. | n.a. | n.a. | n.a. | n.a. | n.a. |
| stability room temperature | | | | | | |
| storage time | 4–5 months | 4–5 months | 8 weeks | 8 weeks | 4 months | 10 weeks |
| classification | 3 | 3 | 3–4 | 2–3 | 4 | 3–4 |
| specific comments | | | slight yellowing | | | |
| stability 50° C. 6 weeks | 2 | 2 | 2 yellowing | 3 | 3–4 | 4 yellowing |
| stability −5° C. 6 weeks | 1 | 1 | 1 | 1 | 2 | 3 |
| stability 5–40° C. 6 weeks | 1 | 1 | slight yellowing | slight yellowing | 3 | 3 yellowing |

| Stability Data (2) | | | | | | |
|---|---|---|---|---|---|---|
| | Ex. 7 | Ex. 8 | Ex. 9 | Ex. 10 | Ex. 11 | Ex. 12 |
| description of product preservative system | double diluted Paraben/sodium benzoate/Phenoxy 0.9% | 75% oil phase of base formula Paraben/sodium benzoate/ Phenoxy 0.9% | only mineral oil Paraben/sodium benzoate/ Phenoxy 0.9% | only mineral oil, double diluted Paraben/sodium benzoate/ Phenoxy 0.9% | total emulsifier 1.0% Paraben/sodium benzoate/ Phenoxy 0.9% | total emulsifier 0.5% Paraben/sodium benzoate/ Phenoxy 0.9% |

-continued

| Stability Data (2) | | | | | | |
|---|---|---|---|---|---|---|
| | Ex. 7 | Ex. 8 | Ex. 9 | Ex. 10 | Ex. 11 | Ex. 12 |
| process | concentrate | concentrate | concentrate | concentrate | whole lotion | whole lotion |
| mean particle size [μm] after manufacturing | n.a. | n.a. | 0.40 | n.a. | n.a. | 0.44 |
| stability 40° C. | | | | | | |
| storage time | 4 weeks | 3 months | 3 months | 4 weeks | 4 weeks | 1 week |
| classification | 7 | 4 | 34 | 7 | 7 | 7 |
| specific comments | | | | | | |
| particle size [μm] after storage at 40° C. | n.a. | n.a. | n.a. | n.a. | n.a. | n.a. |
| stability room temperature | | | | | | |
| storage time | 4 months | 4 months | 4 months | 4 months | 4 months | 4 months |
| classification | 6 | 34 | 4 | 6 | 4 | 7 |
| specific comments | | | | | | |
| stability 50° C. 6 weeks | 1.5 weeks 7 | 4 weeks 7 | 4 weeks 34 | 1–5 weeks 7 | 1 week 7 | 1 week 7 |
| stability −5° C. 6 weeks | 4 weeks 3 | 4 weeks 3 | 4 weeks 2 | 4 weeks 2 | 4 weeks 3 | 4 weeks 2 |
| stability 5–40° C. 6 weeks | 4 weeks 7 | 4 weeks 3 | 4 weeks 3 | 4 weeks 7 | 4 weeks 7 | 1–5 weeks 6 |

| Stability Data (3) | | | |
|---|---|---|---|
| | Ex. 13 | Ex. 14 | Ex. 15 |
| description of product | | | |
| preservative system | Paraben/sodium benzoate/Phenoxy 0.9% | Paraben/sodium benzoate/Phenoxy 0.7% | BKC System |
| process | concentrate | concentrate | concentrate |
| mean particle size [μm] after manufacturing | n.a. | n.a. | n.a. |
| stability 40° C. | | | |
| storage time | 3 months | 3 months | 8 weeks |
| classification | 3 | 3 | |
| specific comments | | | yellowing |
| particle size [μm] after storage at 40° C. | n.a. | n.a. | n.a. |
| stability room temperature | | | |
| storage time | 4.5 months | 4.5 months | 8 weeks |
| classification | 3 | 3 | 3–4 |
| specific comments | | | slight yellowing |
| stability 50° C. | 2 | 2 | 2 yellowing |
| stability −5° C. | 1 | 1 | 1 |
| stability 5–40° C. | 1 | 1 | slight yellowing |

| | Stability Data (4) | | | |
|---|---|---|---|---|
| | Ex. 16 | Ex. 17 | Ex. 18 | Ex. 19 |
| description of product preservative system process | passed at 25° C., 1 pass Paraben/sodium benzoate/Phenoxy 0.9% whole lotion process | passed at 25° C., 2 passes Paraben/sodium benzoate/Phenoxy 0.9% whole lotion process | passed at 50° C., 1 pass Paraben/sodium benzoate/Phenoxy 0.9% whole lotion process | passed at 50° C., 2 passes Paraben/sodium benzoate/Phenoxy 0.9% whole lotion process |
| mean particle size after manufacturing stability 40° C. | 0.55 | 0.37 μm | 0.47 | 0.46 |
| storage time | 3 months | 3 months | 3 months | 3 months |
| classification | 6 | 1 | 5–6 | 4 |
| specific comments | | | | yellowing |
| particle size [μm] after storage at 40° C. stability room temperature | 0.56 | 0.39 | 0.45 | 0.47 |
| storage time | 4.5 months | 4.5 months | 4.5 months | 4.5 months |
| classification | 5 | 3–4 | 5 | 5 |
| specific comments | | | | slight yellowing |
| stability 50° C. 6 | 3 | 2 | 4 | 3 |
| stability −5° C. 4 | 3 | 2 | 3 | 3 |
| stability 5–40° C. | 3 | 1 | 3 | 2 |

The following points should be noted concerning the above stability data tables:

1. In Stability Data table (2), the entries against "description of product" have the following meanings:
   (a) "Double diluted" —quantities of oils and emulsifiers were halved, i.e. to mineral oil 1.0%, dicaprylyl ether 0.5%, caprylic/capric triglyceride 0.5%, ceteareth-12 0.5% and ceteareth-20 0.5%.
   (b) "75% oil phase of base formula" - the quantities of oils and emulsifiers were reduced to 75%.
   (c) "Only mineral oil" —the dicaprylyl ether and caprylic/capric triglyceride were omitted, and 4% mineral oil was used.
   (d) "Only mineral oil, double diluted" —2% mineral oil was present, no dicaprylyl ether or caprylic/capric triglyceride, and 0.5% of each of ceteareth-12 and ceteareth-20.
   (e) "Total emulsifier 1% —the amounts of ceteareth-12 and ceteareth-20 were each reduced to 0.5%, i.e. 1% in total.
   (f) "Total emulsifier 0.5%" —the amounts of ceteareth-12 and ceteareth-20 were each reduced to 0.25%, i.e. 0.5% in total.
   The standard for comparison in (a) to (f) is in each case the composition referred to with reference to Steps 1 to 6 above.

2. In Stability Data table (4), the entries against "description of product" have the following meanings:
   (a) "Passed at 25° C. (50° C.)—homogenized at 25° C. (50° C.)
   (b) "1 pass", "2 passes" —passed once (twice) through the homogenizer.

3. In Example 1, 5, 7 to 13, and 16 to 19, the preservation system consisted of
   Methyl paraben 0.2%
   Propyl paraben 0.1%
   Sodium benzoate 0.4%
   Tetrasodium EDTA 0.1%
   Phenoxyethanol 0.9%.

In Examples 2 and 14 the same system was used, except that the amount of phenoxyethanol was 0.7%.

In Examples 3, 4, 6 and 15, the preservative system consisted of

| | |
|---|---|
| Phenoxyethanol | 0.5% |
| Potassium sorbate | 0.4% |
| Tetrasodium EDTA | 0.1% |
| Benzalkonium chloride | 0.07% |

4. Against the entry "process" the term "concentrate" means that the emulsion was produced by a method as shown in FIG. 1, with a homogenized concentrate being formed (Step 4) and then diluted (Step 5). The term "Whole lotion" means that the emulsion was formed with the whole of the aqueous phase required in the final product already present in Step 4.

5. Mean particle sizes were measured using a Horiba LA-500, i.e. not the LA-910 used to give the other measurements herein. Accordingly, no particular reliance is to be placed on the absolute values of these measurements. The important thing is the comparison between the particle sizes measured after stage storage and those measured after manufacture. As the tables demonstrate, there was virtually no change between one measurement and the other.

As can be seen from the tables, Examples 1 to 6, 9, 13 to 15, 17 and 19 were all satisfactory from a stability point of view. The comparative failure of the other Examples leads to two conclusions.

1. An adequate amount of emulsifier must be present (see Ex. 7, 8, 10, 11, 12).
2. Larger particle sizes leads to greater instability (see Ex. 16 and 18).

It is to be noted, however, that even the Examples described as comparative failures might have some utility, for example where relatively shorter stability times were acceptable, or where stable storage at high temperatures was not required.

By contrast with the overall success of the method of the present invention, attempts by the present inventors to make stable emulsions without a homogenization step, and the small particle size resulting from it, were almost uniformly unsuccessful.

What is claimed:

1. A method of producing a cleansing preparation liquid, comprising the steps of forming a coarse emulsion having a continuous aqueous phase and a discontinuous oil phase, and passing at least substantially the whole of the coarse emulsion through a homogenizer at least once so that the oil phase in the homogenized emulsion consists of particles having a median particle diameter by volume of not more than 1 $\mu$m, the method including incorporating a preservative system in at least the aqueous phase, said preservative system comprising a phenoxyethanol.

2. A method according to claim 1, wherein the step of passing the coarse emulsion through the homogenizer is carried out a plurality of times.

3. A method according to claim 1, wherein homogenization is carried out with a high pressure homogenizer.

4. A method according to claim 3, wherein said pressure is in excess of 100 bar.

5. A method according to claim 3, wherein said pressure is at least 175 bar.

* * * * *

UNITED STATES PATENT AND TRADEMARK OFFICE
CERTIFICATE OF CORRECTION

PATENT NO. : 6,300,301 B1
DATED : October 9, 2001
INVENTOR(S) : Moore et al.

It is certified that error appears in the above-identified patent and that said Letters Patent is hereby corrected as shown below:

Column 2,
Line 24, please delete "mpa.s." and insert therefor -- mPa.s. --.

Column 4,
Line 60, please delete "5".
Line 60, after "spherical." please insert a paragraph break.

Column 9,
Line 46 (TABLE 3, line (51)), in 3$^{rd}$ column of table, please delete "4.4" and insert therefor -- 4.5 --.

Columns 17-18,
9$^{th}$ line of "Stability Data (2)" under "stability 40°C" (classification) in the 4$^{th}$ column (under "3 months"), please delete "34" and insert therefor -- 3-4 --.
17$^{th}$ line of "Stability Data (2)" under "stability room temperature" (classification), in the 3$^{rd}$ column (under "4 months"), please delete "34" and insert therefor -- 3-4 --.
20$^{th}$ line of "Stability Data (2)" under "stability room temperature" (stability 50°C 6 weeks), in the 4$^{th}$ column (under "4 weeks"), please delete "34" and insert therefor -- 3-4 --.
14$^{th}$ line of Stability Data (3) under "stability 40°C" (classification), in the 4$^{th}$ column (under "8 weeks"), please insert -- 1 --.

Columns 19-20,
8$^{th}$ line of Stability Data (4), before "after" please insert -- µm --.
14$^{th}$ line of Stability Data (4) under "stability 40°C" (specific comments), please move "yellowing" from the 5$^{th}$ column to the 4$^{th}$ column.
24$^{th}$ line of Stability Data (4) under "stability room temperature" (specific comments), please move " slight yellowing" from the 5$^{th}$ column to the 4$^{th}$ column.

UNITED STATES PATENT AND TRADEMARK OFFICE
CERTIFICATE OF CORRECTION

PATENT NO. : 6,300,301 B1
DATED : October 9, 2001
INVENTOR(S) : Moore et al.

It is certified that error appears in the above-identified patent and that said Letters Patent is hereby corrected as shown below:

Column 20,
Line 49, please delete "Whole lotion" and insert therefor -- whole lotion --.

Signed and Sealed this

Twenty-first Day of January, 2003

JAMES E. ROGAN
*Director of the United States Patent and Trademark Office*